(12) United States Patent
Larson (10) Patent No.: US 6,575,019 B1
(45) Date of Patent: Jun. 10, 2003

(54) RECIPROCATING DRIVE/PUMP SYSTEM AND RECIPROCATING CAPILLARY VISCOMETER UTILIZING SAME

(75) Inventor: David B. Larson, Broken Arrow, OK (US)

(73) Assignee: Chandler Engineering Company LLC, Broken Arrow, OK (US)

( * ) Notice: Subject to any disclaimer, the term of this patent is extended or adjusted under 35 U.S.C. 154(b) by 0 days.

(21) Appl. No.: 09/760,016

(22) Filed: Jan. 12, 2001

Related U.S. Application Data
(60) Provisional application No. 60/176,267, filed on Jan. 14, 2000.

(51) Int. Cl.⁷ .......................... G01N 11/04; G01N 11/08
(52) U.S. Cl. ...................................... 73/54.04; 73/54.09
(58) Field of Search .............................. 73/54.04, 54.09

(56) References Cited

U.S. PATENT DOCUMENTS

| | | | |
|---|---|---|---|
| 2,649,842 A | | 8/1953 | Caldwell et al. |
| 3,548,638 A | * | 12/1970 | Uchida et al. ............. 73/54.09 |
| 3,710,690 A | | 1/1973 | Dye |
| 4,041,263 A | | 8/1977 | Noeske |
| 4,205,594 A | | 6/1980 | Burke |
| 4,539,837 A | | 9/1985 | Barnaby ..................... 73/54.06 |
| 4,728,344 A | | 3/1988 | Stacy |
| 4,750,351 A | | 6/1988 | Ball |
| 4,836,342 A | | 6/1989 | Wolfe |
| 4,890,482 A | | 1/1990 | Maini |
| 5,009,068 A | | 4/1991 | Clarke |
| 5,011,111 A | | 4/1991 | Nelson et al. |
| 5,315,863 A | | 5/1994 | Cowper |
| 5,383,469 A | | 1/1995 | Vreman et al. |
| 5,847,268 A | | 12/1998 | Ball |
| 5,965,828 A | | 10/1999 | Merriam |

FOREIGN PATENT DOCUMENTS

| | | | | |
|---|---|---|---|---|
| FR | 2398298 | * | 2/1979 | ................. 73/54.04 |
| JP | 62-211542 | * | 9/1987 | ................. 73/54.09 |
| SU | 892039 | | 12/1981 | |
| SU | 1096537 | | 6/1984 | |

\* cited by examiner

*Primary Examiner*—Daniel S. Larkin
(74) *Attorney, Agent, or Firm*—Fellers, Snider, Blankenship, Bailey & Tippens, P.C.

(57) ABSTRACT

A reciprocating pump and a capillary viscometer utilizing the same. Preferably, the inventive reciprocating pump is a syringe pump comprising: a cylinder, an actuated piston, and a floating piston. A chamber is created between the actuated piston and floating piston which may be filled with a pressurant to establish the quiescent pressure of the test fluid. The capillary viscometer comprises: a capillary tube wound about a heated mandrel, a differential pressure transducer, and a reciprocating pump. Test fluid is first pumped at a known rate from a first chamber, through the capillary tube, and into a second chamber. The pump is then reversed and the test fluid is then pumped from the second chamber, back through the capillary tube, and back into the first chamber. The process may be repeated in a continuous, reciprocating manner.

7 Claims, 6 Drawing Sheets

RECIPROCATING DRIVE/PUMP SYSTEM AND RECIPROCATING CAPILLARY VISCOMETER UTILIZING SAME

CROSS REFERENCE TO RELATED APPLICATIONS

This invention claims benefit of copending U.S. Provisional Application Serial No. 60/176,267 filed Jan. 14, 2000.

BACKGROUND OF THE INVENTION

1. Field of the Invention

This invention relates generally to a reciprocating drive/pump system for use in hydraulic applications, and, in a preferred embodiment, for use in a viscometer, which, generally speaking, is a device for measuring the viscosity of fluids. More particularly, but not by way of limitation, the present invention relates to a bidirectional dual piston syringe pump assembly and its use in a reciprocating capillary viscometer.

2. Background

Syringe pumps or cylinder pumps are found in a wide variety of applications, such as manufacturing process control, medical devices, testing instruments, hydraulic systems, and the like. Accumulators are often used in conjunction with such pumps as storage devices to maintain a relatively constant pressure over changing operating conditions and during transient conditions.

Syringe pumps typically comprise a movable piston housed in a cylinder and a rod connecting the piston to a reciprocating driving source, such as a linear actuator. A fluid is drawn into the pump as the piston is moved away from one end of the cylinder and the fluid is pumped from the cylinder as the piston is driven in the other direction. If the diameter of the cylinder is known and the velocity of the piston is known, then the precise flow rate of the fluid may be determined. A bidirectional syringe pump utilizes both sides of the piston such that, as the piston is moved in a direction, fluid is drawn into a first chamber at one end of the cylinder while fluid already present in the a second chamber is pumped out the other end of the cylinder. When the direction of movement of the piston is reversed, fluid is then pumped from the first end while being simultaneously drawn into the other end.

There are many types of viscosity measuring devices. One predominant method for measuring viscosity employs a rotating device that measures the mechanical drag between a rotating member and a stationary member. Rotating viscometers work quite well for many fluids, however, some fluids have properties that actually cause them to climb out of the shear gap, thereby yielding erroneous results, when subjected to testing with such devices. In addition, complications arise with rotating devices when the fluid under test must be under pressure or heated. For example, if the fluid under test must also be under pressure, a rotating seal is required which could impede measuring sensitivity. These types of devices require frequent maintenance of delicate components.

Another type of viscosity measuring device is the reciprocating capillary viscometer. A capillary viscometer is used to determine the viscosity of a fluid by forcing a fluid through a fixed length of capillary tubing with a known diameter, at a known velocity, while measuring the differential pressure across the tube. Mathematical equations which are well known in the art allow calculation of the viscosity of the fluid under test as well as other rheological properties. By periodically reversing the direction of flow through the tubing in a reciprocating manner, continuous measurements may be made on a relatively small sample of fluid.

In the past, reciprocating capillary viscometers have comprised a high pressure chromatography pump, a water or oil bath, capillary tubing, two or more piston accumulators, motor actuated 4-way valves, and a data acquisition and control system. The pump can only move fluid in one direction, so hydraulic fluid is pumped from a reservoir into a first piston accumulator which isolates the fluid under test from the hydraulic fluid. The hydraulic fluid moves the piston thereby forcing the test fluid from the first piston accumulator, through the capillary tube, and into a second piston accumulator. The 4-way valve is used to reciprocatingly apply the hydraulic pressure to each of the piston accumulators. In this way, the fluid under test is first directed to flow from the first accumulator, through the capillary tube in one direction, and into the second accumulator, and then, upon reversal of the 4-way valve, from the second accumulator, back through the capillary tubing in the opposite direction, and back into the first accumulator.

To maintain a uniform temperature of the test fluid, a reciprocating capillary viscometer will typically employ a water or oil bath. While effective, this technique has proven to be large, to be messy, and to have slow heat-up and cool-down performance.

Reciprocating capillary viscometers have typically been large, complex devices requiring frequent and difficult maintenance.

A further limitation of reciprocating capillary viscometers has been the difficulty in loading the fluid under test and cleaning the device between different test fluids.

It is thus an object of the present invention to provide a reciprocating capillary viscometer which is relatively small and less complex, when compared to past devices.

It is a further object of the present invention to provide a method for easily loading the fluid under test and cleaning the viscometer between test fluids.

It is another object of the present invention to provide an improved method for effectively controlling the temperature of the test fluid while measuring rheological properties of such fluid.

It is a still further object of the present invention to provide a bidirectional fluid pump with an integral means for maintaining the fluid pressure within the viscometer.

SUMMARY OF THE INVENTION

The present invention provides a reciprocating capillary viscometer which satisfies the needs and alleviates the problems discussed above. The inventive apparatus preferably comprises; a bidirectional syringe pump; a heated mandrel on which is wound a first tube, a capillary tube and a second tube; a differential pressure transducer for measuring the pressure across the capillary tube; and valves for filling and cleaning the apparatus. When the piston of the pump is moved in a first direction, the test fluid is forced from the first chamber of the pump, through the first tube, through the capillary tube in a first direction, through the second tube, and into the second chamber of the syringe pump. When the pump is moved in the other direction, the test fluid is pumped from the second chamber, through the second tube, through the capillary tube in a second direction, through the first tube and back into the first chamber. A differential pressure gauge is used to measure the pressure drop across the capillary tube while the fluid is moving at a known velocity. Mathematical formulas which are well known in the art allow rheological properties of the test fluid to be determined.

An important aspect of the present invention is the bidirectional syringe pump which has potential applicability in other applications, such as hydraulics, process control, and instrumentation. The syringe pump comprises a cylinder with a driven piston and a floating piston contained therein. The floating piston provides a third pump chamber between the driven piston and the floating piston. This chamber may be pressurized by an external pressure source such that the operating pressure of the hydraulic system may be easily maintained at a pressure established by an external pressure source. When used with the inventive viscometer, the chamber between the driven piston and the floating piston of the inventive bidirectional syringe pump additionally provides a cushion to allow for the expansion or contraction of the test fluid, as the test fluid is heated or cooled, without producing an adverse change in pressure of the test fluid. The floating piston enables the closed loop reciprocating hydraulic circuit to operate at relatively high system pressure with a relatively low horsepower motor driving the syringe pump.

In another aspect of the present invention, there is provided a bidirectional syringe pump driven by a precision, ball-screw actuator.

Further objects, features, and advantages of the present invention will be apparent to those skilled in the art upon examining the accompanying drawings and upon reading the following description of the preferred embodiments.

DETAILED DESCRIPTION OF THE PREFERRED EMBODIMENT

Figure 1:
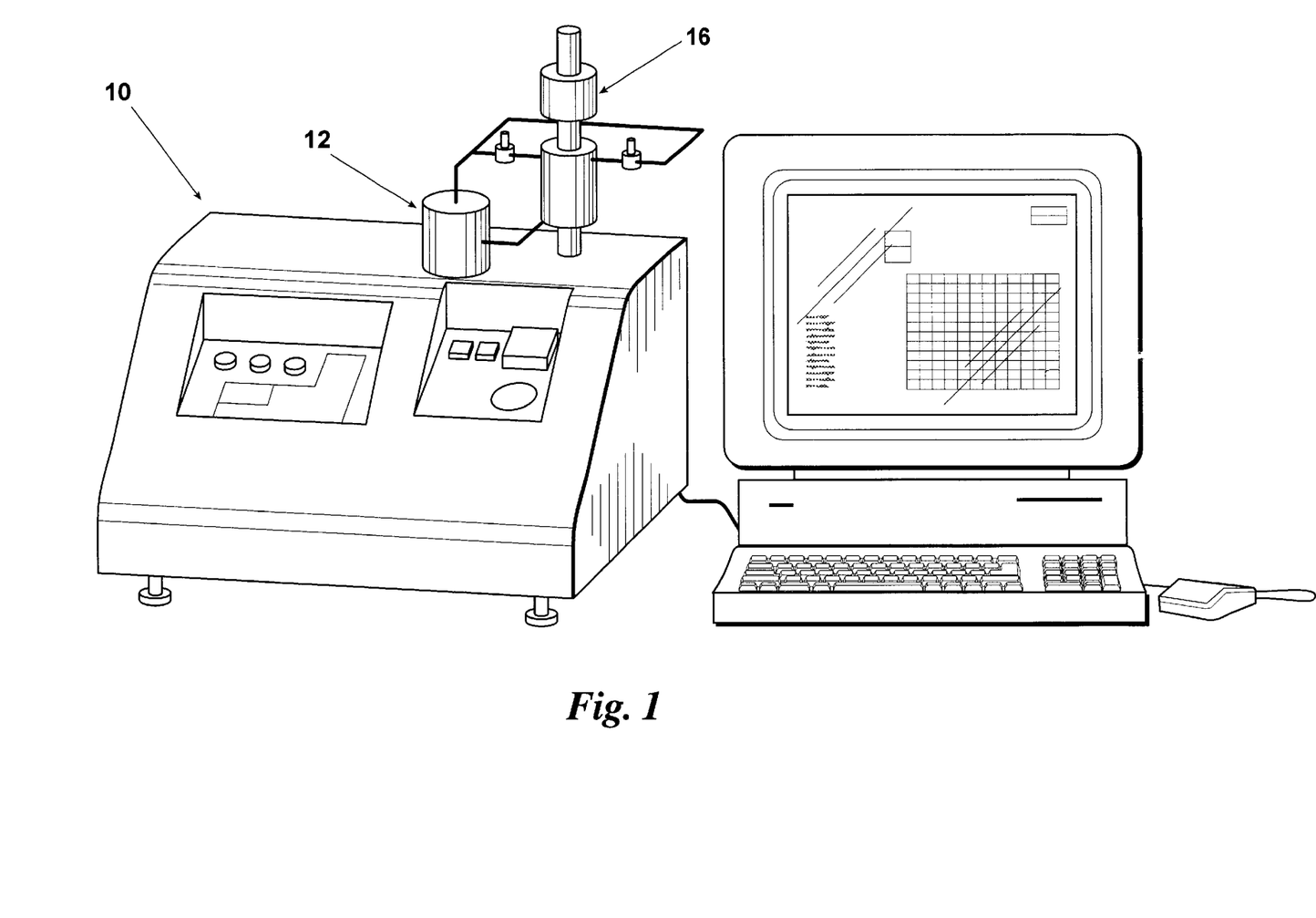
FIG. 1 provides a perspective view of the general environment of the inventive reciprocating capillary viscometer.
Figure 2:
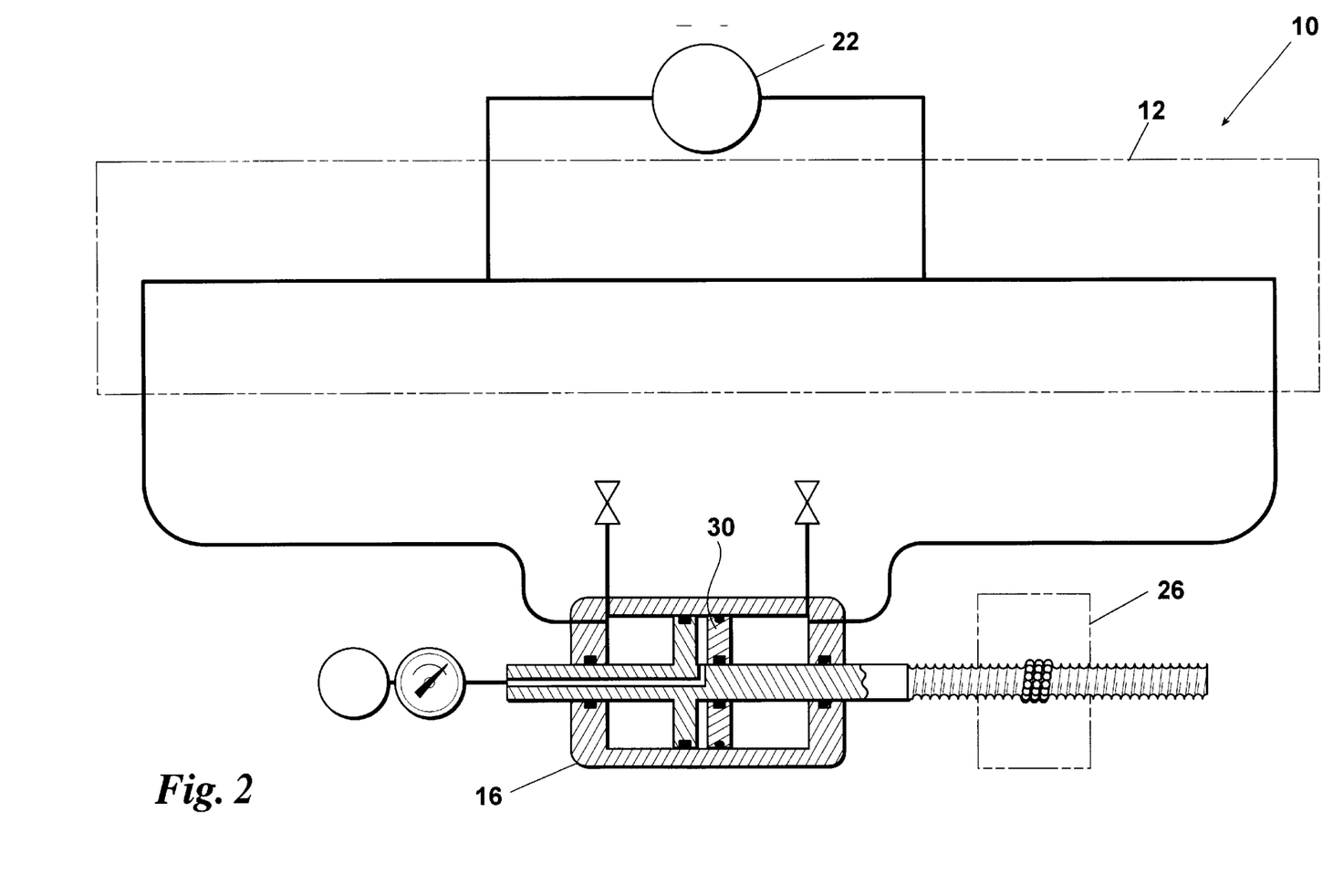
FIG. 2 provides a hydraulic schematic diagram of the inventive reciprocating capillary viscometer.

The preferred embodiment of the inventive, reciprocating capillary viscometer 10 is shown in FIGS. 1 and 2. As best seen in FIG. 2, reciprocating capillary viscometer 10 comprises: a bidirectional syringe pump 16 containing a floating piston 30; a heated mandrel assembly 12; and a differential pressure transducer 22.

Figure 4:
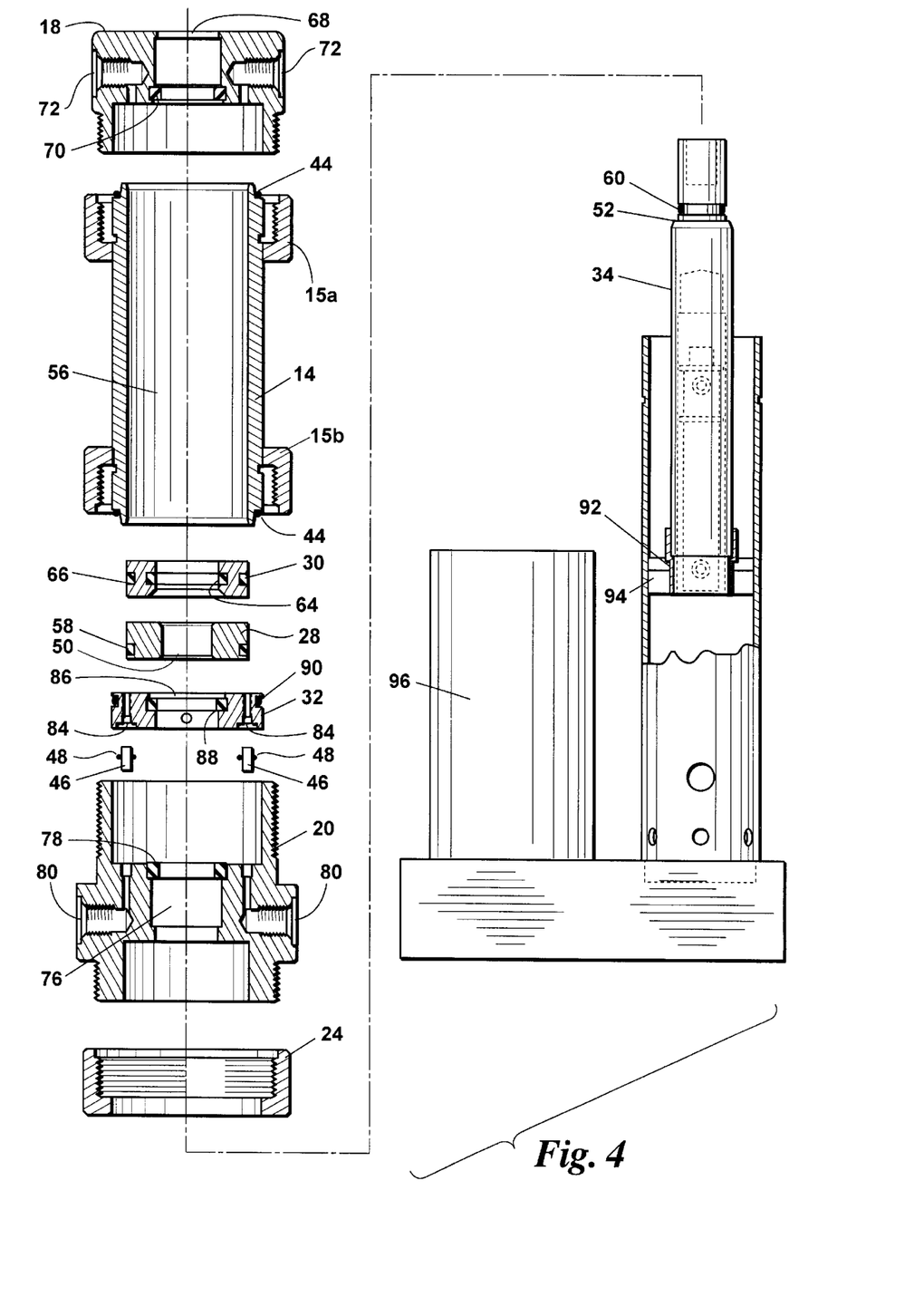
FIG. 4 provides an exploded perspective view of the inventive bidirectional syringe pump incorporated in the inventive reciprocating capillary viscometer.
Figure 5:
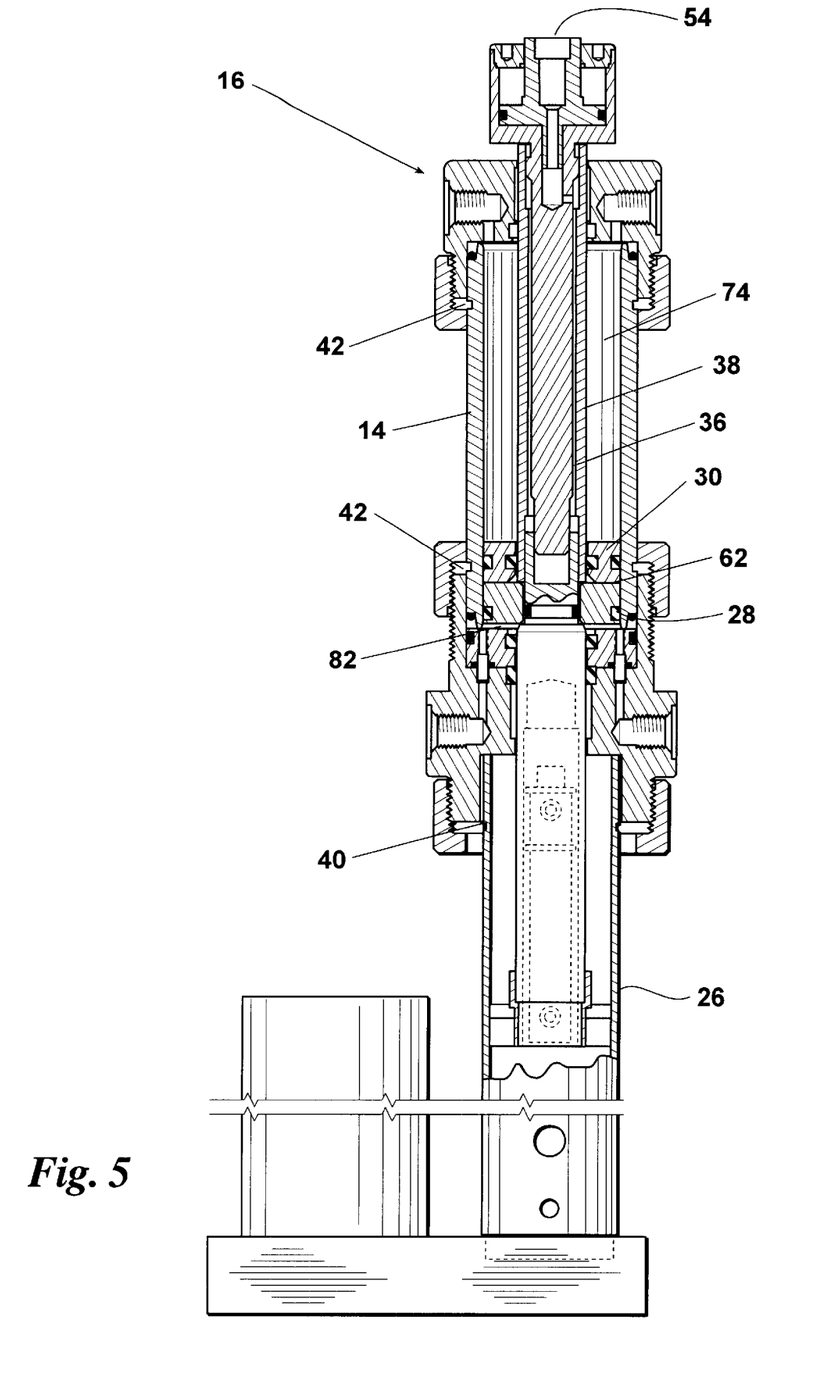
FIG. 5 provides a cutaway elevational view of the inventive syringe pump.

As shown in FIGS. 4 and 5, bidirectional syringe pump 16 preferably comprises: cylinder 14; top and bottom collars 15a and 15b; top cap 18; bottom cap 20; actuator collar 24; actuator assembly 26; actuated piston 28; floating piston 30; seal carrier assembly 32; piston rod 34; tie bolt 36; and sleeve 38.

When pump 16 is assembled, actuator collar 24 is rotatably retained to actuator assembly 26 by snap ring 40 and bottom cap 20 is slidingly received over actuator assembly 26 and secured by collar 24. Bottom and top collars 15a and 15b are rotatably retained to cylinder 14 by snap rings 42. Cylinder 14 is slidingly received in bottom cap 20 and secured by bottom collar 15b. Similarly, cylinder 14 is slidingly received in top cap 18 and secured by top collar 15a. O-rings 44 provide a seal between top cap 18 and cylinder 14 and between bottom cap 20 and cylinder 14. Port inserts 46 and O-rings 48 are sandwiched between seal carrier assembly 32 and bottom cap 20.

Actuated piston 28 contains an aperture 50 which is received over the end of piston rod 34 and is retained against shoulder 52 by sleeve 38 and tie bolt 36 such that any linear movement of rod 34 results in a corresponding movement of actuated piston 28. Actuated piston 28 is sealed against the cylinder wall 56 by quad ring 58 and against rod 34 by quad ring 60.

Floating piston 30 slides freely over sleeve 38. Pressurant enters the external pressure port 54 and flows between the tie bolt 36 and sleeve 38, accessing the gap 62 between floating piston 30 and actuated piston 28. Floating piston 30 is sealed against sleeve 38 by quad ring 64 and against cylinder wall 56 by quad ring 66.

Aperture 68 in top cap 18 provides a passage for sleeve 38 and tie bolt 36. Sleeve 38 is sealed by quad ring 70 as it passes through aperture 68. Ports 72 are provided in top cap 18 for fluids to pass into and out of chamber 74 created between floating piston 30 and top cap 18.

Similarly, bottom cap 20 includes an aperture 76 through which piston rod 34 passes. Rod 34 is sealed by quad ring 78 as it passes through aperture 76. Ports 80 are provided in bottom cap 20 such that fluids may pass into and out of chamber 82 created between actuated piston 28 and seal carrier assembly 32. Seal carrier assembly 32 includes apertures 84 whereby fluids passing through ports 80 may reach chamber 82, and aperture 86 for passage of rod 34. Piston rod 34 is sealed by quad ring 88 as it passes through aperture 86 and seal carrier assembly 32 is sealed against cap 20 by O-ring 90.

Piston rod 34 preferably includes a threaded end 92 which threads into the moving members of actuator assembly 26 whereby rod 34 is linearly driven by actuator assembly 26. Actuator assembly 26 includes a double nut ball screw 94 driven by a bidirectional electric stepper motor 96. The stepper motor may be controlled to provide precise movement of piston rod 34 thereby precisely controlling the volume of test fluid moved by piston 28.

Figure 3A:
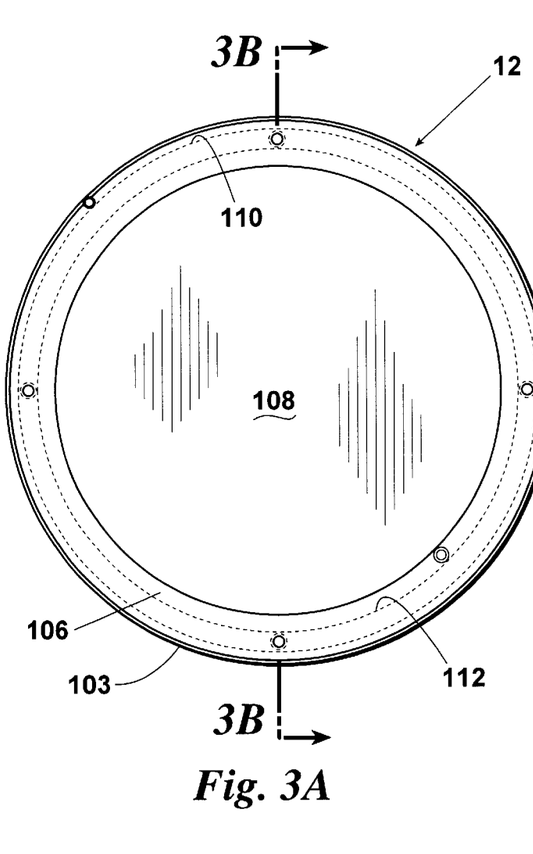
FIG. 3A provides a bottom view of a mandrel assembly as employed in the inventive reciprocating capillary viscometer.
Figure 3B:
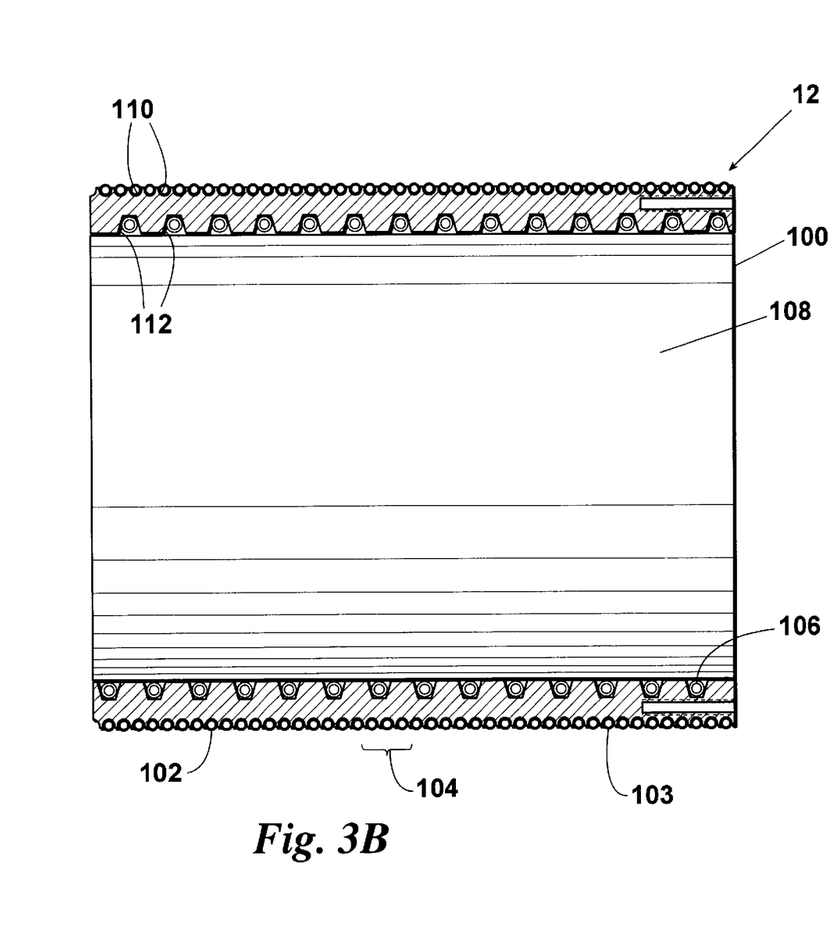
FIG. 3B provides a cutaway side view of the mandrel assembly as used in inventive reciprocating capillary viscometer from perspective 3B shown in FIG. 3A.

Referring now to FIGS. 3A and 3B, heated mandrel assembly 12 comprises: aluminum mandrel 100; first and second tubes 102 and 103; capillary tube 104; cooling coil 106; and electrical resistance heater 108.

Aluminum mandrel 100 includes exterior grooves 110 into which are wound first tube 102, capillary tube 104, and second tube 103. Grooves 110 are shaped such that a very close fit is formed between capillary tube 104 and mandrel 100 for uniform thermal transfer. Cooling coil 106 is wound into interior grooves 112 such that the cooling coil 106 lies entirely below grade. Electrical resistance heater 108 is expanded inside mandrel 100 to form a tight fit and contact the exposed aluminum mandrel 100 between wraps of cooling coil 106. The entire mandrel assembly 12 is insulated to improve temperature uniformity.

Figure 6:
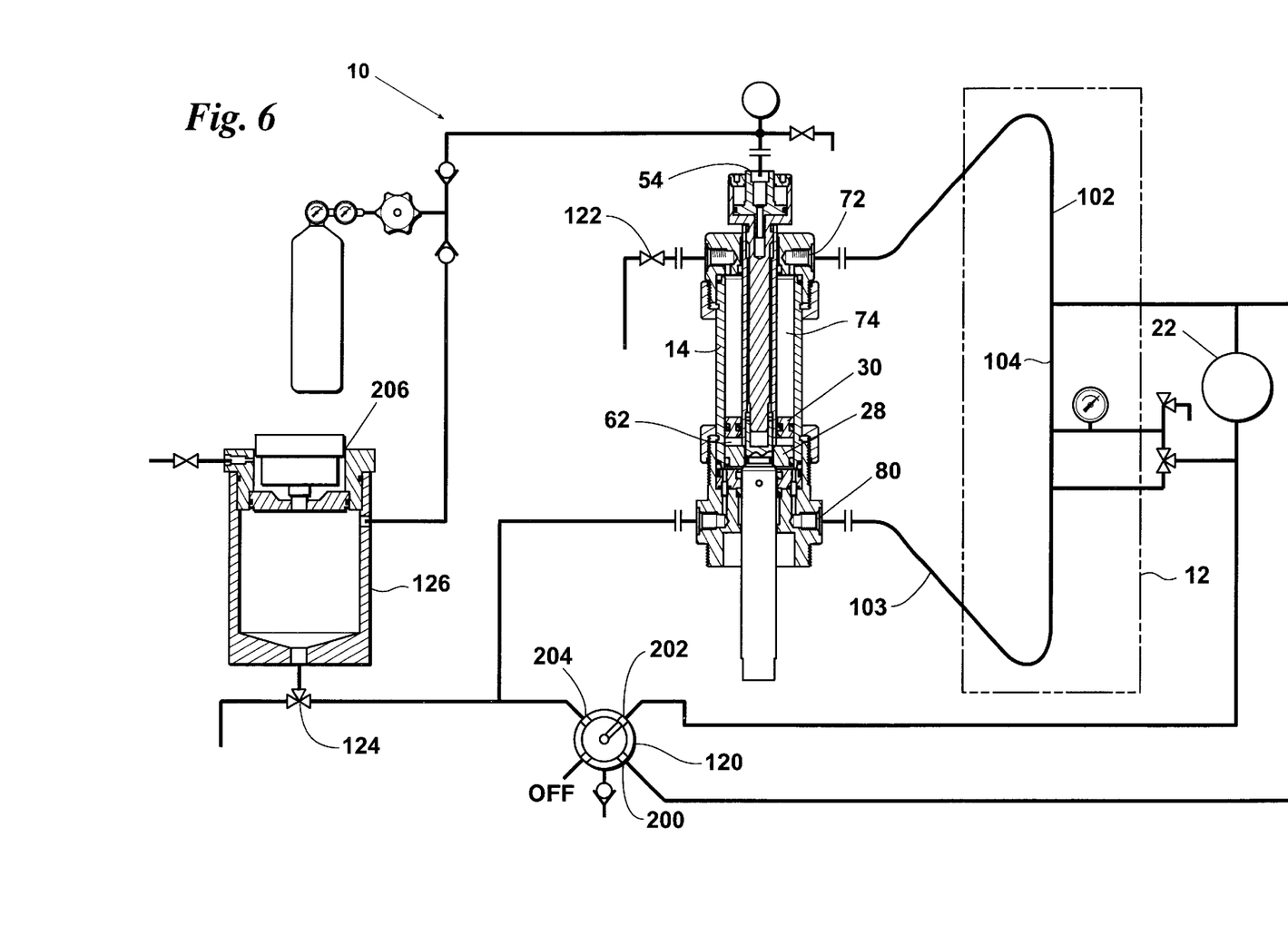
FIG. 6 provides a schematic diagram of the inventive reciprocating capillary viscometer with loader.

Accurate operation of the inventive viscometer 10 requires thorough purging of previous test fluids from the device. The present invention facilitates a simplified purging operation. Referring now to FIG. 6, when loading a test fluid into the inventive viscometer 10, all previous fluids must first be flushed from the system. First, motor 96 (FIG. 4) is driven to place piston 28 at it lowest position within cylinder 14. Valve 122 is opened to relieve any pressure in the system. Pressure is then applied to external port 54 which drives floating piston 30 to the top of cylinder 14 thereby purging top chamber 74 of any fluids through valve 122.

Preferably, a flushing/loading sequence will be followed wherein water or, other flush fluid is introduced at the differential pressure transducer 22 through valve 120 position 200 until uncontaminated flushing fluid can be seen exiting open valve 122. In the same manner, flush fluid is introduced at differential pressure transducer 22 through valve 120 port 202. Again, in the same manner, flush fluid is directed through bottom cap 20, tubes 103, 104, and 102, and top cap 18 through valve 120 port 204. When uncontaminated flush fluid flows from valve 122, the capillary and both ends of the pump 16 are purged and now filled with flush fluid.

Valve 120 is then placed in the closed position thereby preparing the system to receive a test fluid. A test fluid is loaded into loading vessel 126 and lid 206 is closed. Valve 124 is placed in the load position. Pressure is then applied to loader 126 to move test fluid from loader 126 through valve 124, through lower chamber 74 of cylinder 14 out port 80 to fill tubes 103, 104, and 102, and back into top chamber 74 of cylinder 14 through port 72. When uncontaminated test fluid exits valve 122, the capillary and both ends of the pump 16 are filled with test fluid. Valve 122 is then closed.

Next, pressure is applied at external pressure port 54 at the desired operating pressure, thereby pressurizing the system. The purge valve 122 is then opened just enough to allow a few milliliters of test fluid to escape to provide a small chamber 62 filled with pressurant between piston 28 and floating piston 30. This provides a small volume of compressible space to provide for expansion of the test fluid in the capillary.

To test the fluid, the pump 16 is then driven in a reciprocating manner while mandrel assembly 12 is maintained at a desired temperature by electric resistance heater 108. The pressure indicated by differential pressure transducer 22 while the test fluid is in motion is indicative of the viscosity of the test fluid.

As will be understood by those skilled in the art, although the preferred embodiment of the inventive apparatus utilizes a differential pressure transducer, multiple pressure transducers could be used and differential pressure determined in a mathematical step.

As also will be understood by those skilled in the art, although the above-described preferred embodiment of the inventive apparatus has been explained with reference to a pump with integral floating piston, the reciprocating capillary viscometer would work equally well with an external piston accumulator to maintain system pressure.

As will be further understood by those skilled in the art, the diameter of the capillary tube 104 may be varied to allow the investigation of fluids that contain solids or those that have other properties that would favor investigation in a certain capillary diameter or other hydraulic profile over that of another. If two different sizes of capillary tubing are employed in the same capillary loop, a property called "slip" may be investigated.

It will be further understood by those skilled in the art that the inventive bidirectional syringe pump could be used to move fluids for other purposes. For example, such a pump could be used to move cement back and forth to determine thickening time.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention.

What is claimed is:

1. A reciprocation capillary viscometer comprising:
   a bidirectional syringe pump having a first port and a second port;
   a capillary tube having a first end and a second end, said first end in fluid communication with said first port and said second end in fluid communication with said second port; and
   a differential pressure transducer connected between said first end and said second end of said capillary tube,
   wherein said syringe pump reciprocatingly moves a fluid through said capillary tube at a predetermined rate and said differential transducer measures the fluid pressure between said first end and said second end.

2. The reciprocating capillary viscometer of claim 1 further comprising:
   a mandrel;
   a first tube connected to said first end; and
   a second tube connected to said second end,
   wherein said first tube, said capillary tube, and said second tube are formed around said mandrel.

3. The reciprocating capillary viscometer of claim 2 wherein said mandrel further comprises an electric heater.

4. The reciprocating capillary viscometer of claim 3 wherein said mandrel further comprises a cooling coil.

5. The reciprocating capillary viscometer of claim 1 wherein said bidirectional syringe pump further comprises:
   a cylinder having a first end;
   a cap attached over said end, said cap having a first aperture therein;
   a first piston received in said cylinder;
   a second piston received in said cylinder; said second piston having a second aperture therein;
   a rod attached to said first piston, said rod extending through said second aperture in said second piston, and said rod having an end extending through said first aperture in said cap; and
   a linear actuator attached to said end of said rod for driving said rod in a reciprocating manner such that said first piston is moved in a reciprocating manner within said cylinder in response to movement of said linear actuator,
   wherein, said second piston is capable of movement along said rod independent of said first piston such that a chamber is formed between said first piston and said second piston, and
   wherein the volume of said chamber will vary as a result of movement of said second piston relative to said first piston.

6. The reciprocating capillary viscometer of claim 5 wherein said bidirectional syringe pump further comprising a sleeve including an external pressure port, said sleeve received over said rod and received through said first aperture and said second aperture such that said external pressure port is in fluid communication with said chamber.

7. The reciprocating capillary viscometer of claim 6 wherein said bidirectional syringe pump further comprises:
   wherein said cap is a first cap and said first cap further includes a first port, and wherein said chamber is a first chamber, the bidirectional syringe pump further comprising:
      a second cap having a second port;
      a second chamber between said first cap and said second piston; and
      a third chamber between said first piston and said second cap,
   wherein movement of said first piston in a first direction will cause said first piston to draw fluid into said third chamber through said second port and movement of said first piston in a second direction will cause said first piston to expel fluid from said third chamber through said second port, and
   wherein movement of said second piston in said first direction will cause said second piston to expel fluid in said second chamber through said first port and movement of said second piston in said second direction will cause said piston to draw fluid into said second chamber through said first port.

* * * * *